US006491902B2

(12) United States Patent
Shefer et al.

(10) Patent No.: US 6,491,902 B2
(45) Date of Patent: Dec. 10, 2002

(54) CONTROLLED DELIVERY SYSTEM FOR HAIR CARE PRODUCTS

(75) Inventors: Adi Shefer, East Brunswick, NJ (US); Shmuel David Shefer, East Brunswick, NJ (US)

(73) Assignee: Salvona LLC, Dayton, NJ (US)

( * ) Notice: Subject to any disclaimer, the term of this patent is extended or adjusted under 35 U.S.C. 154(b) by 0 days.

(21) Appl. No.: 09/771,752

(22) Filed: Jan. 29, 2001

(65) Prior Publication Data

US 2002/0146379 A1 Oct. 10, 2002

(51) Int. Cl.[7] .............................. A61K 7/06; A61K 9/14
(52) U.S. Cl. ................ 424/70.1; 424/70.11; 424/70.12; 424/401; 424/489; 424/70.27
(58) Field of Search ............................ 424/70.1, 70.11, 424/70.12, 489, 401, 70.27; 510/119; 512/1, 2

(56) References Cited

U.S. PATENT DOCUMENTS

| | | |
|---|---|---|
| 3,980,091 A | 9/1976 | Dasher et al. |
| 4,942,038 A | 7/1990 | Wallach |
| 5,037,818 A | 8/1991 | Sime |
| 5,085,857 A | 2/1992 | Reid et al. |
| 5,124,081 A | 6/1992 | Vanlerberghe et al. |
| 5,198,470 A | 3/1993 | Zysman et al. |
| 5,330,758 A | 7/1994 | Hansenne-Richoux et al. |
| 5,354,564 A | 10/1994 | Borish et al. |
| 5,510,120 A | 4/1996 | Jones et al. |
| 5,518,736 A | 5/1996 | Magdassi et al. |
| 5,556,616 A | 9/1996 | Janchitraponvej et al. .................... 424/70.122 |
| 5,591,449 A | 1/1997 | Bollens et al. |
| 5,599,531 A | 2/1997 | Holcomb |
| 5,658,575 A | 8/1997 | Ribier et al. |
| 5,660,839 A | 8/1997 | Allec et al. |
| 5,660,853 A | 8/1997 | Hansenne-Richoux |
| 5,667,800 A | 9/1997 | De Vringer |

(List continued on next page.)

FOREIGN PATENT DOCUMENTS

| | | |
|---|---|---|
| EP | 0 386 898 A1 | 9/1990 |
| EP | 0 908 174 A2 | 4/1999 |
| WO | WO 95/22311 | 8/1995 |

Primary Examiner—Thurman K. Page
Assistant Examiner—S. Howard
(74) Attorney, Agent, or Firm—Mathews, Collins, Shepherd & McKay, P.A.

(57) ABSTRACT

The present invention is a controlled delivery system that can be incorporated in hair care products such as shampoos, conditioners, hair styling products, and other hair care products to effectively deliver a broad range of active agents and sensory markers, such as fragrances or cooling agents onto the hair. The system also prolongs the release rate of the active agents or sensory markers over an extended period of time, or provides heat triggered release of the active agents and yields a high impact fragrance "burst" upon blow drying the hair or other types of heat treatment. The controlled delivery system of the present invention is a nano-particle, having an average particle diameter of from about 0.01 microns to about 10 microns. The nano-particle comprises hydrophobic polymers and co-polymers, cationic charge boosters in conjunction with cationic surface-active conditioning agents that assist in adhering the particles onto hair. The invention further relates to a controlled delivery system where the release rate of the active ingredients is synchronized with that of a sensory marker to convey to the consumer the product performance.

31 Claims, 3 Drawing Sheets

U.S. PATENT DOCUMENTS

| | | |
|---|---|---|
| 5,741,518 A | 4/1998 | Ribier et al. |
| 5,753,241 A | 5/1998 | Ribier et al. |
| 5,759,526 A | 6/1998 | Simonnet et al. |
| 5,773,611 A | 6/1998 | Zysman et al. |
| 5,780,060 A | 7/1998 | Levy et al. |
| 5,814,343 A | 9/1998 | Jones et al. |
| 5,843,875 A | 12/1998 | Wei et al. |
| 5,851,517 A | 12/1998 | Mougin et al. |
| 5,874,105 A | 2/1999 | Watkins et al. |
| 5,885,564 A | 3/1999 | Zastrow et al. |
| 5,919,487 A | 7/1999 | Simonnet et al. |
| 5,925,364 A | 7/1999 | Ribier et al. |
| 5,945,095 A | 8/1999 | Mougin et al. |
| 5,962,018 A | 10/1999 | Curtis et al. |
| 6,010,707 A | 1/2000 | Philippe et al. |
| 6,013,618 A | 1/2000 | Morelli et al. |
| 6,015,574 A | 1/2000 | Cannell et al. |
| 6,039,936 A | 3/2000 | Restle et al. |
| 6,042,792 A * | 3/2000 | Shefer et al. ............... 422/259 |
| 6,048,520 A | 4/2000 | Hoshowski |
| 6,066,328 A | 5/2000 | Ribier et al. |
| 6,071,535 A | 6/2000 | Hayward et al. |
| 6,083,899 A | 7/2000 | Baker et al. |
| 6,087,322 A | 7/2000 | Morelli et al. |
| 6,126,948 A | 10/2000 | Simonnet et al. |

* cited by examiner

CONTROLLED DELIVERY SYSTEM FOR HAIR CARE PRODUCTS

BACKGROUND OF THE INVENTION

1. Field of the Invention

The present invention relates to a controlled delivery system that can be incorporated into hair care products such as shampoos, conditioners, hair styling products, and other hair care products and that effectively delivers a broad range of active ingredients and sensory markers onto hair, prolongs their release rate over an extended period of time, or provides heat triggered release and high impact fragrance "burst" upon blow drying the hair. The present invention also introduces a novel concept of synchronizing the release of the active ingredients with that of a sensory marker to convey to the consumer the product performance.

2. Description of the Related Art

Consumers are becoming increasingly educated and expect a high level of sophistication and multi functionality in their hair care products. They expect the product not only to clean, but also condition, nourish, and provide a lasting impression of clean hair and freshness. Consumer acceptance of hair care products is determined not only by the performance achieved with these products but the perception and aesthetics associated therewith. There is also a need to convey to the consumer the product performance and effectiveness (i.e., the hair is clean, the hair is being conditioned and nourished, etc.). Fragrance is an important aspect of the successful hair care products and they can also be utilized, in addition to imparting an aesthetically pleasing odor, to convey the consumer the product performance.

Fragrance creation for hair care products is restricted not only by considerations such as availability and cost, but also by compatibility of the fragrance ingredients with other components in the product composition and the ability of the fragrance ingredients to deposit onto the hair and survive the wash and rinse process. Furthermore, a large amount of fragrance is often lost during the rinse and drying processes, even when the hair is air-dried. Practice has shown that when current commercial hair care products are used, very little of the fragrance is actually substantive onto the hair.

Publications in the prior art indicate attempts to fulfill the foregoing needs to increase the deposition of active ingredients and fragrances onto hair and to hinder or delay their release rate so that the hair is healthier and remains aesthetically pleasing for a prolonged length of time.

A conventional approach that has been described employs emulsions, liposomes, and other lipid vesicles to deposit the active ingredients onto the hair. See U.S. Pat. Nos. 4,942,038; 5,124,081; 5,198,470; 5,330,758; 5,510,120; 5,518,736; 5,591,449; 5,658,575; 5,660,853; 5,741,518; 5,753,241; 5,759,526; 5,773,611; 5,814,343; 5,874,105; 5,885,564; 5,925,364; 6,010,707; 6,015,574; 6,039,936; 6,066,328; 6,071,535; and 6,126,948. These types of systems have the limitation of being unstable, and can only be used for encapsulation of certain types of materials. Stability has limited the use of liposomes for controlled delivery, both in terms of shelf life and after administration.

U.S. Pat. No. 5,354,564 discloses personal care products comprising an aqueous dispersion of particles of silicone wherein said particles have a surface modifier adsorbed on the surface thereof in an amount sufficient to achieve a particle size of less than about 400 nanometers (nm). The particles of this invention contain a discrete phase of silicone having a surface modifier adsorbed on the surface thereof. Suitable surface modifiers can preferably be selected from known organic and inorganic excipients. Such excipients include various polymers, low molecular weight oligomers, natural products and surfactants. Preferred surface modifiers include nonionic and anionic surfactants.

U.S. Pat. No. 5,599,531 discloses the uses of inorganic charged colloidal silica as a carrier system for hair care products. The penetration or absorption of water, oils, collagen, and other materials into the hair is greatly increased by adding a small quantity of inorganic charged colloidal silica to provide an aqueous suspension of the charged colloidal silica particles along with the material to be absorbed into the hair. In coloring hair, dye components can be absorbed into the hair without the use of alkaline solutions which damage the hair, and in perming hair, the disulfide bonds in the hair can be broken by tension caused by swelling due to water absorption in the hair, again without the use of damaging alkaline solutions. It is believed that the porosity and stable hydration of the hair can be varied through altering the electrostatic charge on the hair. The aqueous suspension of charged silica particles applied to the hair appears to alter this charge.

U.S. Pat. No. 5,660,839 discloses incorporating deformable hollow particles into cosmetic and/or dermatological compositions containing fatty substances, for markedly reduce or eliminate the sticky and/or greasy feel attributed to these fatty substances. Preferably, the particles are in the form of hollow microspheres or microbeads, having a particle size ranging from 1 micron to 250 microns, and comprising a copolymer of vinylidene chloride, acrylonitrile and a (meth)acrylate co monomer.

U.S. Pat. No. 5,667,800 discloses an aqueous suspension of solid lipoid nanoparticles, comprising at least one lipid and preferably also at least one emulsifier, for topical application to the body. The nano-particles disclosed are preferably non-ionic and the emulsifiers used in the processing of these particles are preferably chosen from the groups of polyoxyethylene alkyl ethers and sorbitan esters. The particles have a mean particle size of between 50–1000 nm and their concentration is between 0.01–60 wt %, by weight of the suspension. A medicament can be incorporated into the continuous phase of the suspension or in a vehicle, which is added to the suspension. The invention further provides manufacturing methods for the aqueous suspension.

U.S. Pat. No. 5,780,060 discloses microcapsules with a wall of crosslinked plant polyphenols and compositions containing them. The microcapsules are obtained by the interfacial crosslinking of plant polyphenols, particularly flavonoids. When incorporated in a composition such as a cosmetic, pharmaceutical, dietetic or food composition, these microcapsules make it possible to prevent any impairment of this composition, in particular any color modification, while at the same time preserving the activity, especially the anti-free radical and/or antioxidizing activity, of the plant polyphenols, particularly the flavonoids.

U.S. Pat. Nos. 5,851,517 and 5,945,095 disclose compositions including a dispersion of polymer particles in a non-aqueous medium. A dispersion of surface-stabilized polymer particles can be used in a non-aqueous medium, in a cosmetic, hygiene or pharmaceutical composition. The dispersions may, in particular, be in the form of nano-particles of polymers in stable dispersion in a non-aqueous medium. The nano-particles are preferably between 5 and 600 nm in size, given that beyond about 600 nm, the particle dispersions become much less stable. The polymers used can be of any nature, such as radical polymers, polycondensates or polymers of natural origin. These polymers may, in particular, be crosslinked. Among the non-film-forming polymers described are vinyl or acrylic radical copolymers or homopolymers, which are optionally crosslinked, preferably having a Tg of greater than or equal to 40 degree C, such as polymethyl methacrylate, polystyrene, or poly-tert-butyl acrylate.

U.S. Pat. Nos. 5,759,526 and 5,919,487 disclose nanoparticles coated with a lamellar phase based on silicone surfactant and compositions containing them. The nanoparticles, and in particular nanocapsules, provided with a lamellar coating obtained from a silicone surfactant, can be used in a composition, in particular a topical composition, for treatment of the skin, mucosae, nails, scalp and/or hair. Nanoparticles ranging in size from 10 to 1000 nm are composed of a polymer encapsulating an oily phase and coated with a lamellar coating, wherein the lamellar coating comprises at least one silicone surfactant containing at least a oxyethylenated and/or oxypropylenated chain. The nanoparticles preferably range in size from 10 to 600 nm. The polymers constituting the nanoparticles can be biodegradable or non-biodegradable polymers. Poly-L- and -DL-lactides and polycaprolactones are especially preferred as biodegradable polymers. Among non-biodegradable polymers, copolymers of vinyl chloride and vinyl acetate and copolymers of methacrylic acid and methacrylic acid methyl ester are especially preferred.

U.S. Pat. Nos. 6,013,618 and 6,087,322 disclose the use of pro-accords as a method to enhance fragrance performance from personal care products. Typically the pro-accords are comprised of orthoesters, ketals, acetals, orthocarbonates which release two or more fragrance raw materials upon hydrolysis.

U.S. Pat. No. 6,042,792 discloses a controlled, time-release microparticulate active and bioactive compositions (including perfuming compositions) for targeted delivery to services such as skin, hair and fabric and the environment proximate thereto, where the active and bioactive materials have a calculated log P values of between 1 and 8 (P being the n-octanol-water partition coefficient). Such compositions include the active or bioactive material in single phase, solid solution in a wax or polymer matrix also having coated thereon and/or containing a compatible surfactant. Also described are processes and apparatus for preparing such compositions. The emphasis of U.S. Pat. No. 6,042,792 is in engineering the fragrance formulation and thus limiting the type of fragrances that can be used with the system.

U.S. Pat. No. 6,048,520 discloses a transparent leave-on hair treatment composition including capsules of a water insoluble hair-treating compound encased in a shell material, such as gelatin or acacia gum. The capsules have a diameter of about 425 to about 2800 microns and are broken during application of the hair treatment composition to hair or by combing the hair after application of the hair treatment composition. The aqueous leave-on composition is applied to the hair and the water insoluble hair-treating compound is released from the capsules to treat the hair. The shell disintegrates into sufficiently small residual particles such that the physical and esthetic properties of the hair, like shine and combability, are retained.

Cationic deposition polymers have been conventionally used to enhance deposition of certain nonvolatile components from shampoos and other personal cleansing compositions. For example, U.S. Pat. Nos. 5,037,818 and 5,085,857 describe the use of cationic guar gum to enhance the deposition of antidandruff particles and insoluble nonvolatile silicone, respectively. Deposition polymers have also been proposed to enhance the deposition of sunscreen materials from a shampoo composition. In EP 386,898 a cationic polygalactomannan gum derivative is used. WO 95/22311 describes the use of certain cationic polymers to increase the deposition of nonvolatile benefit agents which include silicones, fats and oils, waxes, hydrocarbons, fatty acids and fatty alcohols, lipids, vitamins and sunscreens.

U.S. Pat. No. 6,083,899 discloses fabric softener compositions that have enhanced softening benefits. The fabric softeners consist of a fabric softener active in combination with a cationic charge booster. The cationic charge boosters are suitable for use with any fabric softener active, preferably with diester and diamide quaternary ammonium (DEQA) compounds.

Similar phenomena were also observed for hair care products. U.S. Pat. 3,980,091 discloses that the pretreatment of hair on the human head, preceding shampooing the hair with anionic type hair shampoos, and with compositions for effecting such pretreatment, to obtain highly improved manageability of the hair after shampooing and with improved fullness, combability and other desired properties of the hair. The pretreatment compositions utilize readily water-soluble quaternary ammonium compounds, particularly in combination with certain agents, notably polyethylenimines and N-ethanolacetamide, and desirably together with various supplemental ingredients.

The prior art of which applicant is aware does not set forth a controlled delivery system for hair care products that is highly substantive onto hair, sustain the release rate of active ingredients and a sensory marker or provide heat triggered release of the active agents and high impact fragrance "burst" upon blow drying the hair.

SUMMARY OF THE INVENTION

The present invention relates to an improved controlled delivery system for hair care products, such as, shampoo, conditioner, hair styling products, and other hair care products, comprising nano-particles formed of hydrophobic polymers and copolymers in combination with cationic charge booster and cationic conditioning agents to improve the system deposition onto hair. The nano particles of the present invention can include active ingredients and sensory markers.

The controlled delivery system of the present invention is a nan-particle having a solid inner core with cationic exterior that confers several advantages as compared with conventional microspheres, liposhperes, and vesicles, including high dispersibility in an aqueous medium, and a release rate for the entrapped substance that is controlled by the hydrophobic material barrier properties as well as the barrier properties of the hydrophilic layer of cationic surfactant. There are also many advantages over other suspension-based delivery systems. Nano-particles have increased stability as compared to emulsion-based delivery systems, including vesicles and liposomes, and are more effectively dispersed than most suspension based systems. Further, the substance to be delivered does not have to be soluble in the vehicle since it can be dispersed in the solid matrix. The nano-particles of the present invention also have a lower risk of reaction of substance to be delivered with the vehicle than in emulsion systems because the vehicle is a solid inert material. Moreover, altering either, or both, the inner solid core or the outer surfactant layer can manipulate the release rate of the substance from the nano-particles. Nano-particles are also easier to prepare than structured vehicles such as liposphere, and are inherently more stable.

The nano-particles of the present invention have an improved mechanism to enhance the deposition of the particles onto hair. The highly cationic charge density characterizing the nano-particles of the present invention, achieved by the use of cationic conditioning agents in conjunction with cationic charge booster improves the deposition of these particles onto the hair and prevents them from being washed off during the rinse process. The nano-particles of the present invention are believed to attach to the hair surfaces via a complexing interaction between the cationic charge group on the particles and the proteinaceous portion of the hair and thus predispose or condition the surface of the hair so that the nano-particles will then adhere to the surface.

In one embodiment, the present invention provides an improved controlled delivery system for hair care products, that improves the substantivity of active ingredients and sensory markers onto hair by means of bringing the particles onto the hair through treating the hair with hair care products comprising the nano-particles of the present invention. In the hair care industry, the term "substantivity" refers to the deposition of the active ingredients or sensory markers (i.e., fragrance) on the hair and the retention and perception of the fragrance on surfaces treated with hair care product. Particles comprising cationic charge boosters and the cationic conditioning agents either in the particle composition, or at the particles outer surface, were observed to be highly substantive on surfaces such as skin, hair, and fabric.

The delivery system of the present invention enhances the deposition of active agents and sensory markers onto hair, prolongs their release rate over an extended period of time, or release them upon heat treatment such as blow drying the hair. In addition, the release rate of the active agents is synchronized with that of a sensory marker (i.e., fragrance) to convey to the consumer the product performance.

It has been found that increasing the cationic charge density of the particles through the use of cationic charge boosters in conjunction with cationic conditioning agents enhances the adhesion of the particles onto hair. In addition, by incorporating cationic surface-active agents into the nano-particles composition, the system provides improved compatibility of a wide range of active agents and sensory markers in the delivery system, and increases the substantivity of actives that are currently not substantive on hair.

The prior art of which applicant is aware does not set forth a controlled release system which synchronizes the release rate of the active ingredients with that of fragrances or sensory markers to convey to the consumer the product performance.

The nano-particles of the present invention are characterized by:

(i) protection of the active ingredients and sensory markers during storage, until needed.;
(ii) enhanced deposition of the active ingredients and sensory markers onto hair;
(iii) the release rate of the active ingredients is synchronized with that of a sensory marker;
(iv) prolong release of the active ingredients and sensory markers over an extended period of time; or
(v) heat triggered release of the active ingredients and high impact fragrance "burst" upon blow drying the hair.

The invention also provides a process for producing the nano-particles of the present invention that comprises the steps of:

a) heating the hydrophobic polymers and copolymers to a temperature above the material melting point;
b) dissolving or dispersing the active agents and/or the sensory markers into the melt;
c) dissolving or dispersing the cationic conditioning agents and/or cationic charge boosters in the melt;
d) dissolving or dispersing the cationic conditioning agents, cationic charge boosters, and/or a co-surfactant in the aqueous phase and heating it to a temperature above the melting point of the melt;
e) mixing the hot melt with the aqueous solution to form a suspension;
f) high shear homogenization of the suspension at a temperature above the melting temperature until a homogeneous fine suspension is obtained; and
g) cooling the suspension to ambient temperature to form a fine dispersion.

It is believed that the highly substantive cationic charge booster in conjunction with the cationic conditioning agents in the particles surface becomes associated, in use, with the hair and assist in adhering the particles onto hair through both particle entrainment and electrostatic interactions. The highly cationic charge density of the nano-particles, achieved by the use of cationic conditioning agents in conjunction with cationic charge booster, improves the deposition of these particles onto the hair and prevents them from being washed off during the rinse process. The nano-particles are believed to attach to the hair surfaces via a complexing interaction between the cationic charge group on the particles and the proteinaceous portion of the hair and thus predispose or condition the surface of the hair so that the nano-particles will then adhere to the surface. The hydrophobic polymers and copolymers sustain the diffusion rate of the fragrance through the particles and enable the release of the active ingredients and sensory markers over an extended period of time, or during heat treatment such as blow drying the hair.

Hair treated with hair care products, such as shampoo, conditioners, and the like, comprising the nano-particles of the present invention were observed to exhibit high level of fragrance (high odor intensity) in both the wet and the dry state and fragrance perception on the dry hair has been observed over an extended period of time up to about 24 hours.

The present invention also provides a cost effective controlled delivery system that improves fragrance performance from hair care products.

The invention still further provides hair care products such as shampoo, conditioner, hair styling products, and other hair care products, comprising the nano-particles of the present invention.

BRIEF DESCRIPTION OF THE DRAWINGS

For a better understanding of the present invention, reference may be made to the accompanying drawings.

DETAILED DESCRIPTION

Figure 1:
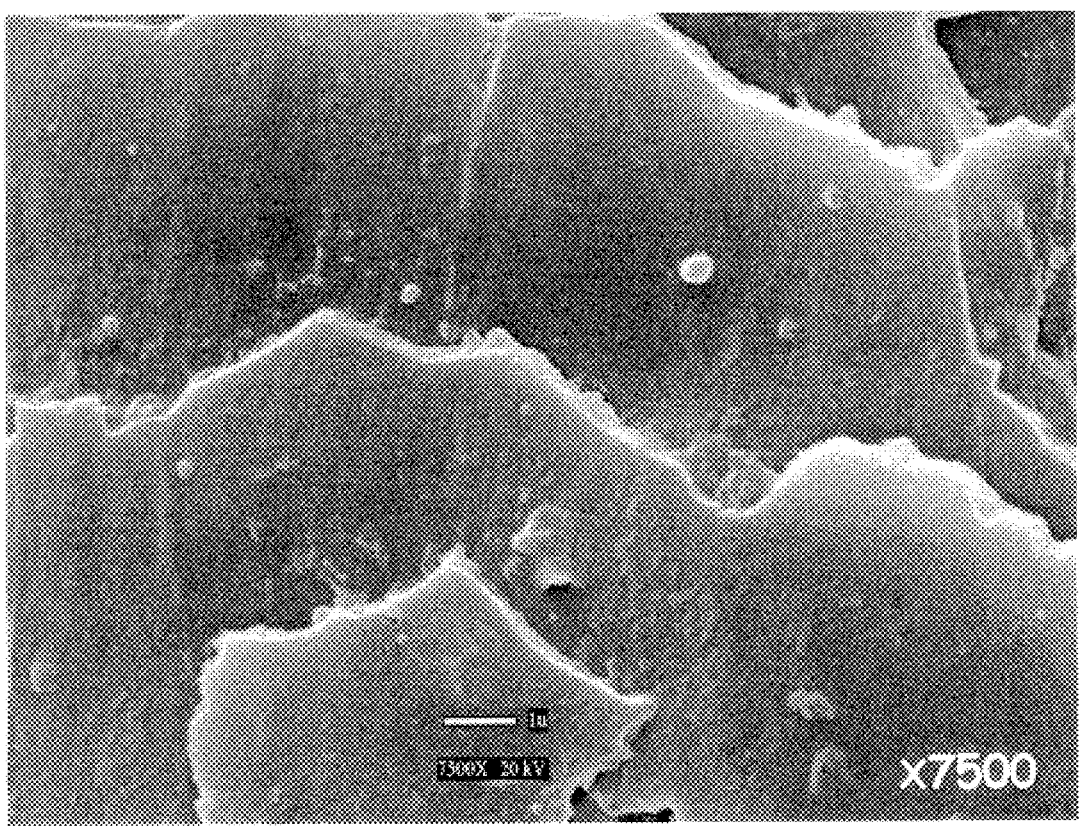
FIG. 1 is a scanning electron microscopy image of hair, treated with a shampoo comprising the nano-particle of the present invention, magnified 7500 times.

Reference will now be made in greater detail to a preferred embodiment of the invention, an example of which is illustrated in the accompanying drawings. Wherever possible, the same reference numerals will be used throughout the drawings and the description to refer to the same or like parts.

The present invention features a method of controlling the release rate of fragrance that can be incorporated in a hair care product, over an extended period of time, or yields a high impact fragrance "burst" upon heat treatment such as blow drying the hair. Heat activation is defined as some change that is mediated by use of the composition of the invention with heat, from styling appliances such as a blow dryer, curling iron, hot curler, hot brush, hot comb, hot rollers, crimper, or hair dryer. From internal testing of various appliances this average temperature can range on the "hot" setting to be between 50 degree C to 60 degree C. The carrier system of the present invention comprises substantially solid nano-particles in combination with a cationic charge booster and cationic conditioning agents. The term "particles" is intended to describe solid, substantially spherical particulates. It will be appreciated that other particle shapes can be formed in accordance with the teachings of the present invention.

The particles of the present invention have a predetermined particle size. The low end of the useful size range of the particles is limited by undue loss of volatile active agents and sensory markers from the particle. The permeation rate of the active agents and sensory markers from the particle is proportional to particle size such that the smaller particles, the faster the rate that the active agent or sensory marker is being released. The nano-particles employed herein have an average size (diameter) range of from about 0.01 micron to about 10 microns. Preferably, the particle size of the particles is in the range from about 0.01 microns to about 1 micron, and particles within this range are efficiently entrained on hair. This linear dimension for any individual particle represents the length of the longest straight line joining two points on the surface of the particle.

The hydrophobic core of the nano-particles contains the active ingredients and sensory markers. The active agents and the sensory markers can be either hydrophilic or hydrophobic. Preferably the nano-particles have an average particle size in the range from about 0.01 microns to about 10 microns and have a melting point in the range from about 45 degrees C to about 100 degrees C. The nano-particle preferably comprises from about 1% to about 95% by weight hydrophobic polymers, hydrophobic copolymers, or mixtures thereof, from about 0.01% to about 10% by weight cationic charge booster, from about 0.01% to about 20% by weight cationic conditioning agents, from about 1% to about 70% by weight active agents, and from about 1% to about 70% by weight sensory markers. The nano-particles can be incorporated into any type of hair care products, preferably in shampoo and conditioning compositions.

A continuous phase of the nano-particle dispersion formed is aqueous, and can contain additional components such as antioxidants, preservatives, microbicides, buffers, osmoticants, cryoprotectants, and other useful additives or solutes. The additional components are present in an amount from about 1% to about 30% by weight of the aqueous dispersion.

I. CATIONIC CHARGE BOOSTERS

The controlled delivery system of the present invention comprises a cationic charge booster. Suitable cationic charge boosters are described in U.S. Pat. No. 6,083,899 hereby incorporated by reference into this application. The preferred cationic charge boosters of the present invention are described herein below.

I.a. Quaternary Ammonium Compounds

A preferred composition of the present invention comprises at least about 0.1%, preferably from about 0.1% to about 10%, more preferably from about 0.1% to about 5% by weight, of a cationic charge booster having the formula:

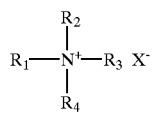

wherein $R_1$, $R_2$, $R_3$, and $R_4$ are each independently $C_1$–$C_{22}$ alkyl, $C_3$–$C_{22}$ alkenyl, $R_5$—Q —$(CH_2)_m$—, wherein $R_5$ is $C_1$–$C_{22}$ alkyl, and mixtures thereof, m is from 1 to about 6; X is an anion. Preferably $R_1$ is $C_6$–$C_{22}$ alkyl, $C_6$–$C_{22}$ alkenyl, and mixtures thereof, more preferably $R_1$ $C_{11}$–$C_{18}$ is alkyl, $C_{11}$–$C_{18}$ alkenyl, and mixtures thereof; $R_2$, $R_3$, and $R_4$ are each preferably $C_1$–$C_4$ alkyl, more preferably each $R_2$, $R_3$, and $R_4$ are methyl.

Alternatively, $R_1$ can be a $R_5$—Q—$(CH_2)_m$— moiety wherein $R_5$ is an alkyl or alkenyl moiety having from 1 to 22 carbon atoms, preferably the alkyl or alkenyl moiety when taken together with the Q unit is an acyl unit. For example Q can be derived from a source of triglyceride selected from tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof An example of a cationic charge booster comprising a $R_5$—Q—$(CH_2)_m$—moiety has the formula:

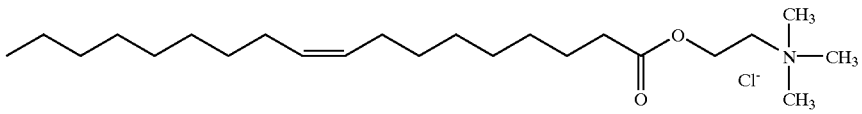

wherein $R_5$—Q—represents oleoyl units and m is equal to 2.

Preferably X is a softener compatible anion, such as the anion of a strong acid. For example, X can be chloride, bromide, methylsulfate, ethylsulfate, sulfate, nitrate and mixtures thereof More preferably X is chloride and methyl sulfate.

I.b. Polyvinyl Amines

A preferred composition according to the present invention contains at least about 0.1%, preferably from about 0.1% to about 10%, more preferably from about 0.1% to about 5% by weight, of one or more polyvinyl amines charge boosters having the formula

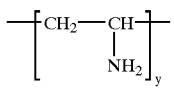

wherein y is from about 3 to about 10,000, preferably from about 10 to about 5,000, more preferably from about 20 to about 500. Polyvinyl amines suitable for use in the present invention are available from BASF under the name Lupasol® LU 321. The greater number of amine moieties per unit weight on the polyvinyl amines provides preferred substantial charge density.

I.c. Polyalkyleneimines

A preferred composition of the present invention comprises at least about 0.1%, preferably from about 0.1% to about 10%, more preferably from about 0.1% to about 5% by weight, of a polyalkyleneimine charge booster having the formula:

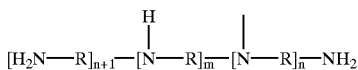

wherein the value of m is from 2 to about 700 and the value of n is from 0 to about 350. Preferably the compounds of the present invention comprise polyamines having a ratio of m:n that is at least 1:1 but may include linear polymers (n equal to 0) as well as a range as high as 10:1, preferably the ratio is 2:1. When the ratio of m:n is 2:1, the ratio of primary-:secondary:tertary amine moieties of —RNH$_2$, —RNH, and —RN moieties, is 1:2:1. R can be C$_2$–C$_8$ alkylene, C$_3$–C$_8$ alkyl substituted alkylene, and mixtures thereof. Preferably R is ethylene, 1,2-propylene, 1,3-propylene, and mixtures thereof, and more preferably ethylene. R radicals serve to connect the amine nitrogens of the backbone.

Optionally, one or more of the polyvinyl amine backbone —NH$_2$ unit hydrogens can be substituted by an alkyleneoxy unit having the formula:

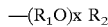

wherein R$_1$ is C$_2$–C$_4$ alkylene; R$_2$ is hydrogen, C$_1$–C$_4$ alkyl, and mixtures thereof; and x is from 1 to 50. In one embodiment or the present invention the polyvinyl amine is reacted first with a substrate which places a 2-propyleneoxy unit directly on the nitrogen followed by reaction of one or more moles of ethylene oxide to form a unit having the general formula:

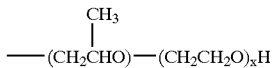

wherein x has the value of from 1 to about 50. Substitutions such as the above are represented by the abbreviated formula PO—EO.sub.X —. However, more than one propyleneoxy unit can be incorporated into the alkyleneoxy substituent.

The preferred polyamine cationic charge boosters of the present invention comprise backbones wherein less than about 50% of the R groups comprise more than 3 carbon atoms. The use of two and three carbon spacers as R moieties between nitrogen atoms in the backbone is advantageous for controlling the charge booster properties of the molecules. More preferred embodiments of the present invention comprise less than about 25% moieties having more than 3 carbon atoms. Yet more preferred backbones comprise less than about 10% moieties having more than 3 carbon atoms. Most preferred backbones comprise about 100% ethylene moieties.

The cationic charge boosting polyamines of the present invention comprise homogeneous or non-homogeneous polyamine backbones, preferably homogeneous backbones. For the purpose of the present invention the term "homogeneous polyamine backbone" is defined as a polyamine backbone having R units that are the same such as, all ethylene. However, this definition does not exclude polyamines that comprise other extraneous units comprising the polymer backbone that are present due to an artifact of the chosen method of chemical synthesis. For example, it is known to those skilled in the art that ethanolamine may be used as an "initiator" in the synthesis of polyethyleneimines, therefore a sample of polyethyleneimine that comprises one hydroxyethyl moiety resulting from the polymerization "initiator" would be considered to comprise a homogeneous polyamine backbone for the purposes of the present invention.

For the purposes of the present invention the term "non-homogeneous polymer backbone" refers to polyamine backbones that are a composite of one or more alkylene or substituted alkylene moieties, for example, ethylene and 1,2-propylene units taken together as R units.

However, not all of the suitable charge booster agents belonging to this category of polyamine comprise the above described polyamines. Other polyamines that comprise the backbone of the compounds of the present invention are generally polyalkyleneamines (PAA's), polyalkyleneimines (PAI's), preferably polyethyleneamine (PEA's), or polyethyleneimines (PEI's). Polyethyleneimines suitable for use in the present invention are available from BASF under the trade name Lupasol® such as Lupasol™PR8515, having an average molecular weight of 1,800, Lupasol™ Waterfree; Lupasol™P, Lupasol™PR971L; Lupasol™PL; Lupasol™SKA. Ethoxylated polyethyleneimines suitable for use in the present invention are available from BASF under the name Lupasol™SC®-61B. A common polyalkyleneamine (PAA) is tetrabutylenepentamine. PEA's can be obtained by reactions involving ammonia and ethylene dichloride, followed by fractional distillation. The common PEA's obtained are triethylenetetramine (TETA) and tetraethylenepentamine (TEPA). Above the pentamines, such as, the hexamines, heptamines, octamines and possibly nonamines, the cogenerically derived mixture does not appear to separate by distillation and can include other materials such as cyclic amines and particularly piperazines.

I.d. Poly-Quaternary Ammonium Compounds

A preferred composition of the present invention comprises at least about 0.1%, preferably from about 0.1% to about 10%, more preferably from about 0.1% to about 5% by weight, of a cationic charge booster having the formula:

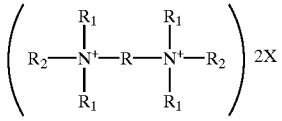

wherein R is substituted or unsubstituted C$_2$–C$_{12}$ alkylene, substituted or unsubstituted C$_2$–C$_{12}$ hydroxyalkylene; each R$_1$ is independently C–C$_4$ alkyl, each R$_2$ is independently C–C$_{22}$ alkyl, C$_3$–C$_{22}$ alkenyl, R$_5$—Q—(CH$_2$)$_m$—, wherein R$_5$ is C$_1$–C$_{22}$ alkyl, C$_3$–C$_{22}$ alkeny, and mixtures thereof; m is from 1 to about 6; Q is a carbonyl unit as described above and mixtures thereof, X is an anion.

Preferably R is ethylene and R$_1$ is preferably methyl or ethyl, more preferably methyl. Preferably at least one R$_2$ is $C_1$–$C_4$ alkyl, more preferably methyl. Most preferably at least one $R_2$ is $C_{11}$–$C_{22}$ alkyl, $C_{11}$–$C_{22}$ alkenyl, and mixtures thereof.

Alternatively $R_2$ is a $R_5$—Q—$(CH_2)_m$— moiety wherein $R_5$ is an alkyl moiety having from 1 to 22 carbon atoms, preferably the alkyl moiety when taken together with the Q unit is an acyl unit derived from a source of triglyceride selected from the group consisting of tallow, partially hydrogenated tallow, lard, partially hydrogenated lard, vegetable oils, partially hydrogenated vegetable oils, such as, canola oil, safflower oil, peanut oil, sunflower oil, corn oil, soybean oil, tall oil, rice bran oil, and the like and mixtures thereof.

An example of a fabric softener cationic booster comprising a $R_5$—Q—$(CH_2)_m$— moiety has the formula:

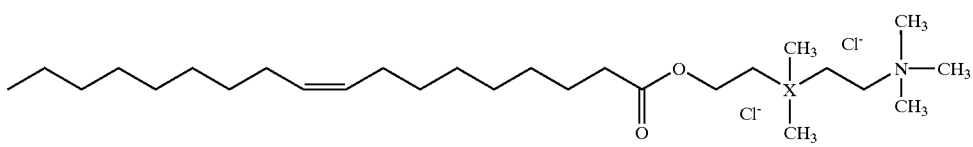

wherein $R_1$ is methyl, one of the $R_2$ units is methyl and the other of the $R_2$ unit is $R_5$—Q—$(CH_2)_m$— wherein $R_5$—Q— is an oleoyl unit and m is equal to 2. X is a softener compatible anion, such as an anion of a strong acid. For example, X can be chloride, bromide, methylsulfate, ethylsulfate, sulfate, nitrate and mixtures thereof. More preferably chloride and methyl sulfate.

II. CATONIC CONDITIONING AGENTS

The carrier system of the present invention can comprise any of the cationic hair conditioning agents known in the art. The conditioning agents can include imidazolinium. Other quaternary ammonium salt hair conditioning compounds suitable for use are described in "Cationic Surfactants", Surfactant Science series, Vol. 34, edited by Richmond J. M., Marcel Dekker Inc., 1990, which are incorporated herein by reference.

Cationic conditioning agents of the present invention, are believed to attach to hair via a complexing interaction between the cationic portion of the cationic conditioning agent and the proteinaceous portion of the hair and thus predispose or condition the surface of the hair so that the nano-particles will then adhere to the surface. Surface active materials that are capable of strong bonding to the negatively charged and hydrophilic surfaces of hair include various straight-chain alkylammonium compounds, cyclic alkylammonium compounds, petroleum derived cationics, and polymeric cationic materials. A preferred cationic conditioning agent is Behenamidopropyl hydroxyethyl dimonium chloride and a fatty quaternary ammonium salt, available as Incroquat Behenyl HE, from Croda Inc. Parsippany, N.J.: Quaternary ammonium salt, available as Quaternium-82 and STEPANQUAT™ ML, commercially available from Stepan, and polyquaterium-24 (Quatrisoft polymer LM-200, from Amerchol Corporation, Edison, new Jersey). It was found to adhere to skin and hair. The cationic conditioning agents also stabilize the outer surface of the hydrophobic core component of the nano-particles, thereby promoting a more uniform particle size. The cationic conditioning agent can be present in a proportion of about 0.01% to about 20% by weight of the suspension, preferably about 0.05% to about 2%.

II.a.) Straight-chain Alkylammonium Compounds

One group of cationic conditioning agents useful for enhancing the deposition of the nano-particles of the present invention onto hair are quaternary ammonium compounds. Quaternary ammonium salts useful herein also include dialkyldimethylammonium chlorides wherein the allkyl groups have from 12 to 22 carbon atoms. The alkyl groups can be derived from long-chain fatty acids, such as hydrogenated tallow fatty acid. Tallow fatty acid gives rise to quaternary compounds wherein the substituted groups contain predominantly from 16 to 22 carbon atoms. Examples include ditallow dimethyl ammonium chloride, ditallow dimethyl ammonium methyl sulfate, dihexadecyl dimethyl ammonium chloride, di(hydrogenated tallow)dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl)dimethyl ammonium chloride, and stearyl dimethyl benzyl ammonium chloride. Preferred quaternary ammonium salts useful herein include ditallow dimethyl ammonium chloride, dicetyl dimethyl ammonium chloride, stearyl dimethyl benzyl ammonium chloride, cetyl trimethyl ammonium chloride, tricetyl methyl ammonium chloride, and mixtures thereof Di(hydrogenated tallow)dimethyl ammonium chloride (Quatemium-18) is a particularly preferred quaternary ammonium salt, and is available from the Sherex Chemical Company, Inc. as Adogen®442 and Adogen®442–100P.

Salts of primary, secondary and tertiary fatty amines can also be used as cationic conditioning agents. The alkyl groups of such amines preferably have from 12 to 22 carbon atoms, and can be substituted or unsubstituted. Secondary and tertiary amines are preferred; and tertiary amines are particularly preferred. Examples of useful amines include stearamido propyl dimethyl amine, diethyl amino ethyl stearamine, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Examples include stearylamine hydrochloride, soyamine chloride, stearylamine formate, N-tallowpropane diamine dichloride and stearamidopropyl dimethylamine citrate.

Preferred conditioning agents are quaternary ammonium salts. Preferred quaternary ammonium salts include dialkyldimethylammonium chlorides, wherein the alkyl groups have from 12 to 22 carbon atoms. These alkyl groups may be derived from long-chain fatty acids, such as hydrogenated tallow fatty acid. Tallow fatty acid gives rise to quaternary compounds wherein the substituted groups predominantly contain from 16 to 18 carbon atoms. Examples of preferred quaternary ammonium salts include: di(hydrogenated)tallow dimethyl ammonium chloride; dicetyl dimethyl ammonium chloride; tricetyl methyl ammonium chloride; cetyl trimethyl ammonium chloride; stearyl dimethyl benzyl ammonium chloride; and mixtures thereof Most preferred is dicetyl dimethyl ammonium chloride.

Other more preferred conditioning agents are: behenalkonium chloride; behentrimonium chloride; behenalkonium methosulfate; behentrimonium methosulfate; behenamidopropylamine oxide; behenopropyl dimethylamine; behenamidopropyl dimethylamine; behenamidopropyl dimethylamine behenate; behenamidopropyl ethyldimonium ethosulfate; behenamidopropyl PG-dimonium chloride; behenamine; and behenamidopropyl hydroxyethyl dimonium chloride.

II.b.) Cyclic Alkylammonium Compounds

Another preferred group of compounds of cationic conditioning agents useful for enhancing deposition of nanoparticles onto the hair include a class of surface-active quaternary ammonium compounds in which the nitrogen atom carrying the cationic charge is part of a heterocyclic ring. Suitable compounds, for example, are as follows: laurylpyridinium chloride or bromide; tetradecylpyridinium bromide; and cetylpyridinium halide, wherein the halide is chloride, bromide or fluoride.

II.c.) Petroleum Derived Cationic Compounds

Typical basic amines useful for the present invention are derived from petroleum-based raw materials such as olefins, paraffins, and aromatic hydrocarbons and include compounds with at least one aliphatic carbon chain containing six or more carbon atoms attached to the nitrogen. Amine salts, diamines, amidoamines, alkoxylated amines, and their respective quaternary salts are suitable for the present invention. Preferred compounds of this type include tallow or coco alkyl substituted 1,3-propylene diamines sold by Witco under the names of "Adogen" and "Emcol" and similar diamines sold by Akzo under the name "Duomeen" and polyethenoxy derivatives sold by Akzo under the names of "Ethomeen" and "Ethoduomeens".

II.d.) Cationic Polymers

Cationic polymers suitable for use in the present invention are selected from the group of polyquaternium 32, polyquatemium 3, cocodimonium hydroxypropyl hydrolyzed collagen, cocodimonium hydroxypropyl hydrolyzed hair keratin, cocodimonium hydroxypropyl hydrolyzed hair keratin, cocodimonium hydroxypropyl hydrolyzed keratin, cocodimonium hydroxypropyl hydrolyzed wheat protein, cocodimonium hydroxypropyl oxyethyl cellulose, guar hydroxypropyltrimonium chloride, lauryldimonium hydroxypropyl hydrolyzed collagen, lauryldimonium hydroxypropyl hydrolyzed wheat protein, lauryldimonium hydroxypropyl oxyethyl cellulose, polyquaternium 4, polyquaternium 10, polyquaternium 24, steardimonium hydroxyethyl cellulose, steardimonium hydroxypropyl hydrolyzed collagen, steardimonium hydroxypropyl hydrolyzed wheat protein, steardimonium hydroxypropyl oxyethyl cellulose, steardimonium hydroxyethyl hydrolyzed collagen, polymethacrylamidopropyl trimonium chloride, polyquaternium 2, polyquaternium 6, polyquaternium 7, polyquaternium 11, polyquaternium 16, polyquatemium 17, polyquaterium 18, polyquaternium 22, polyquaterium 24, polyquatenium 27, polyquaternium 28, polyquaternium 31, polyquaterium 39, polyquaternium 41, polyquaternium 42, quatemium 80, and quaternized hydrolyzed wheatiprotein/dimethicone phosphocopolyol copolymer. The preferred cationic conditioning agent are polyquaterium-24 available under the name Quatrisoft® polymer LM-200, from Amerchol Corporation.

Also suitable, for the purpose of this invention, are cationic derivatives of polysaccharides such as dextran, starch or cellulose, for example, diethylaminoethyl cellulose ("DEAE-cellulose"). Further examples of suitable materials are the cationic guar derivatives such as those sold under the trade name JAGUAR® by Celanese-Hall.

A further preferred group of compounds, which comprises a class of water-insoluble polymers, having nitrogen atoms in their molecules, are quaternary polymers of quaternary ammonium type, betaine type, pyridylpyridinium type or vinylpyridinium-type. Examples are as follows poly(vinylbenzylmethyllaurylammonium chloride); poly(vinylbenzylstearylbetaine); poly(vinylbenzyllaurylpyridylpyridinium chloride); poly(vinylbenzylcetylammonylhexyl ether) and quaternized polyoxyethyleneated long chain amines, with the general formula $RN(CH_3)[(C_2H_4O)x\,H]_2$ (+) A(–), where A(–) is generally chloride or fluoride, x is a number from 1 to 20, and R is $C_{8-22}$-alkyl.

In a preferred embodiment, the cationic conditioning agents are cetyl trimethylammonium chloride, behenamidopropyl hydroxyethyl dimonium chloride, and polyquaterium-24, Quatemium-82, and polyquaterium-24, and Quatrisoft polymer LM-200, available from Amerchol.

III. MATRIX MATERIALS

The matrix materials for forming the particles of the carrier system of the present invention comprise any substantially water-insoluble polymers and copolymers compatible with and miscible with the active agents or fragrance composition used in the present invention and harmless or beneficial to the hair when dispersed and melted on to them. Preferably, the matrix material provides barrier properties to the active agents and the fragrance compositions low toxicity and irritancy, stability, and high loading capacity for the active agents. Examples of suitable hydrophobic polymers and copolymer for use as the matrix material include polyethylene homopolymers A-C®1702; A-C®617, A-C®617A, and A-C®15, commercially available from AlliedSignal Inc.; PERFORMALENE™ PL available from Baker Pertolite Co.; polyethylene homopolymer commercially available from New Phase Technologies; ethylene-acrylic acid copolymers A-C®540, A-C®540A, and A-C®580 commercially available from AlliedSignal Inc.; polyamides having a molecular weight in the range of from about 6,000 up to about 12,000, for example, MACROMEL™6030 manufactured by the Henkel Ag. of Dusseldorf, Germany; VERSALON™1135 polyamide polymer available commercially from General Mills, Inc.; polyethylene-vinyl acetate copolymers; silicon copolymer modified waxes, for example; candelilla/silicon copolymer, ozokerite/silicon copolymer (SP 490 and SP 1026), and other silicon copolymer modified natural and synthetic waxes, commercially available from Strahl & Pitsch Inc., reaction products of silicon copolymers with synthetic and natural waxes, for example siliconyl candelilla, and siliconyl synthetic paraffin LMS, commercially available from Koster Keunen Inc.

Synthetic and natural waxes can also be utilized as hydrophobic materials for the carrier system of the present invention. Examples are natural, regenerated, or synthetic waxes including: animal waxes, such as beeswax; lanolin and shellac wax; vegetable waxes such as carnauba, cutina, sugar cane, rice bran, and bayberry wax; mineral waxes such as petroleum waxes including paraffin and microcrystalline wax; and mixtures thereof Other hydrophobic compounds which may be used include fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol; solid hydrogenated castor and vegetable oils; hard paraffins; hard fats; and mixtures thereof Other hydrophobic compounds which may be used in the present invention include triglycerides, preferably of food grade purity or better, which may be produced by synthesis or by isolation from natural sources. Natural sources may include animal fat or vegetable oil, such as, soy oil, a source of long chain triglycerides (LCT). Other suitable triglycerides are composed predominantly of medium length fatty acids (C10–C18), denoted medium chain triglycedrides (MCT). The fatty acid moieties of such triglycerides can be unsaturated, monounsaturated or polyunsaturated. Mixtures of triglycerides having various fatty acid moieties are also useful for the present invention. The core can comprise a single hydrophobic compound or a mixture of hydrophobic compounds. Hydrophobic materials are known to those skilled in the art and are commercially available, as described in the list of suitable carrier materials in Martindale, The Extra Pharmacopoeia, The Pharmaceutical Press, $28^{th}$ Edition pp 1063–1072 (1982).

It is preferred that the particles used in the present invention have a melting point in the range from about 45 degrees C to about 100 degrees C, preferably from about 50 degrees C to about 80 degrees C. The melting point of the particles is usually a function of the carrier matrix employed. It should be understood that it is the melting point of the particle rather than of the carrier matrix that is important for use of the carrier system of the present invention.

IV. CO-SURFACTANTS

In an embodiment of the present invention improved stability is achieved by incorporation of an amphiphilic and/or nonionic co-surfactant. Co-surfactants can be either natural compounds, such as phospholipids and cholates, or nonnatural compounds such as: polysorbates, which are fatty acid esters of polyethoxylated sorbitol (Tween); polyethylene glycol esters of fatty acids from sources such as castor oil (Emulfor); polyethoxylated fatty acid, stearic acid (Simulsol M-53); Nonidet; polyethoxylated isooctylphenol/ formaldehyde polymer (Tyloxapol); poloxamers, poly (oxyethylene)poly(oxypropylene) block copolymers (Pluronic); polyoxyethylene fatty alcohol ethers (Brij); polyoxyethylene nonylphenyl ethers (Triton N); polyoxyethylene isooctylphenyl ethers (Triton X); and SDS. Mixtures of surfactant molecules, including mixtures of surfactants of different chemical types, are acceptable. Surfactants should be suitable for pharmaceutical administration and compatible with the drug to be delivered.

Particularly suitable surfactants include phospholipids, which are highly biocompatible. Especially preferred phospholipids are phosphatidylcholines (lecithins), such as soy or egg lecithin. Other suitable phospholipids include phosphatidylglycerol, phosphatidylinositol, phosphatidylserine, phosphatidic acid, cardiolipin, and phosphatidylethanolamine. The phospholipids can be isolated from natural sources or prepared by synthesis. Phospholipid surfactants are believed usually to form a single monolayer coating of the hydrophobic core, The co-surfactant can comprise less than about 5%, usually less than about 1%, preferably less than about 0.1%, relative to the weight of the core component of the nanoparticle. In some embodiments, one or more co-surfactants may be present.

V. ACTIVE AGENTS

The active agents can be cosmetic, dermatological, and pharmaceutical active agents. Suitable active agents include ceramides, vitamins, antioxidants, free radical scavengers, moisturizing agents, antiseborrhoeic agents, anti-UV agents, keratolytic agents, anti-inflammatory agents, refreshing agents, melanoregulators, liporegulators, antiseborrhoeic agents, anti-ageing agents, keratolytic agents, antibacterial agents, anti-dandruff agents, agents for combating hair loss, hair dyes, hair bleaches, reducing agents for permanent waves, hair conditioners and nutrients, cicatrizing agents, vascular protectors, antibacterial agents, anti fungal agents, skin conditioners, immunomodulators, nutrients and essential oils, retinoids, anesthetics, surfactants, emulsifiers, stabilizers, preservatives, antiseptics, emollients, lubricants, humtectants, analgesics, enzymes, pigments, dyes, hydroxy acids, such as, alpha hydroxy acids, and beta hydroxy acids, emollients, medications, antibiotics, repellants, attractants such as, pheromones, fragrances, sensory markers such as cooling agents of menthol derivatives, hyaluronic acid and its salts, elastin, hydrolysates, primrose oil, jojoba oil, epidermal growth factor, soybean saponins, mucopolysaccharides, and mixtures thereof.

V.a.) Ceramides

Ceramides which are preferred according to the invention are: N-linoleoyldihydrosphingosine; N-oleoyldihydrosphingosine; N-palmitoyldihydrosphingosine; N-stearoyldihydrosphingosine; and N-behenoyldihydrosphingosine;

V.b.) Vitamins

Various vitamins can be included as active agents of the present invention. For example, vitamin A and derivatives thereof, vitamin $B_2$, biotin, pantothenic acid, vitamin K, vitamin D, vitamin E, vitamin C and mixtures thereof may be used.

V.c.) Sunscreens

Sunscreen agents are desirable active agents of the present invention. The sunscreen agent is preferably incorporated into the aqueous composition. The term "sunscreen agent" as used herein defines ultraviolet ray-blocking compounds exhibiting absorption within the wavelength region between about 290 and about 400 nm. Sunscreens can be classified into five groups based upon their chemical structure: para-amino benzoates; salicylates; cinnamates; benzophenones; and miscellaneous chemicals including menthyl anthranilate and digalloyl trioleate. Inorganic sunscreens can also be used including titanium dioxide, zinc oxide, iron oxide and polymer particles such as polyethylene, polymethylmethacrylates and polyamides. Preferred materials include p-aminobenzoic acid and its derivatives, anthranilates; salicylates; cinnamates; coumarin derivatives; azoles; and tannic acid and its derivatives.

A wide variety of conventional sunscreening agents are suitable for use in the present invention as described in Segarin et al., at Chapter VIII, Pages 189 et seq., of "Cosmetics Science and Technology", the disclosure of which is incorporated herein by reference. Suitable sunscreening agents include, for example: p-aminobenzoic acid, its salts and derivatives, anthranilates, salicylates, cinnamic acid derivatives, dihydroxycinnamic acid derivatives, trihydroxycinnamic acid derivatives, hydrocarbons, dibenzalacetone and benzalacetophenone, naphthosulfonates, dihydroxy-naphthoic acid and its salts, o- and p-hydroxybiphenyldisulfonates, coumarin derivatives, diazoles quinine salts, quinoline derivatives, hydroxy or methoxy substituted benzophenones, uric and vilouric acids, tannic acid and its derivatives, hydroquinone, benzophenones, agents for UVA and UVB protection, and the like.

V.d.) Anti Inflammatory Agents

Anti-inflammatory can be included in the compositions of the invention to enhance photo protection benefits, particularly from UVA. Steroidal anti-inflammatory agents can include hydrocortisone; non-steroidal anti-inflammatory agents can include oxicans, salicylates, acetic acid derivatives, fenamates, propionic acid derivatives, pyrazoles, substituted phenyl compounds, 2-naphthyl containing compounds, and the natural anti-inflammatory illustrated by aloe-vera. Other non-steroidal anti-inflammatory agents include anti-inflammatory drugs including flurbiprofen, ibuprofen, indomethacin, piroxicam, naproxen, antipyrine, phenylbutazone and aspirin. Suitable anti-inflammatory agents are described in U.S. Pat. No. 5,487,884, the entire contents of which are incorporated herein by reference.

V.e.) Antioxidants

Antioxidants useful for the present invention include ascorbic acid. Other suitable antioxidants include vitamin E, tocopheryl acetate, betaglucan, coenzyme Q1O, representative formula $CH_3C_6(O)_2(OCH_3)_2$ )$CH_2CH:C(CH_3)CH_2$ !$_n$ H, butylated hydroxytoluene (BHT), BHA, superoxide dismutose, propylgallate, and the like. It will be appreciated that other conventional antioxidants can be used in the present invention.

V.f) Drugs

Suitable drugs which can be administered in the delivery system of the present invention include but are in no way limited to anti-bacterial agents such as thimerosal, chloramine, boric acid, phenol, iodoform, chlorhexidine and other oral antiseptics, beta-lactam antibiotics, for example cefoxitin, n-formamidoyl thienamycin and other thienamycin derivatives, tetracyclines, chloramphenicol, neomycin, gramicidin, kanamycin, amikacin, sismicin and tobramycin; anti-inflammatory steroids such as cortisone, hydrocortisone, beta-methasone, dexamethasone, fluocortolone, prednisolone, triamcinolone and the like. The biologically active ingredient my also be one or more antibiotics, such as penicillin, polymyxin B, vancomycin, kanamycin, erythromycin, niddamycin; metronidazole, spiramycin and tetracycline.

V.g.) Sensory Markers

The present invention can include sensory markers such as fragrances and cooling agents such as menthol derivatives. Preferably the sensory markers are synchronized with the release of the active agents to convey to the consumer the product performance, provide long lasting odor and signal that a new application of the product is needed.

The fragrance ingredients and compositions of this invention can be conventional ones known in the art. Selection of any perfume component, or amount of perfume, is based on functional and aesthetic considerations. Typical examples of usable fragrance and flavor compounds discussed hereinafter, along with their odor characters, and their physical and chemical properties, are described in "Perfume and Flavor Chemicals (Aroma Chemicals)", Steffen Arctander, published by the author, 1969, and in "Common Fragrance and flavor Materials—Preparation, Properties and Uses", Kurt Bauer and Dorotea Garbe, published by VCH Verlagsgesellschaft mbH, 1985, incorporated herein as reference.

V.h.) Preservatives

Preservatives can be incorporated into the present invention to protect against the growth of potentially harmful microorganisms. While it is in the aqueous phase that microorganisms tend to grow, microorganisms can also reside in the anhydrous or oil phase. As such, preservatives, which have solubility in both water and oil, are preferably employed in the present compositions. Suitable traditional preservatives for compositions of this invention are alkyl esters of parahydroxybenzoic acid. Other preservatives, which can be used include hydantoin derivatives, propionate salts, and a variety of quaternary ammonium compounds.

Particularly preferred preservatives are methylparaben, imidazolidinyl urea, sodium dehydroacetate, propylparaben, trisodium ethylenediamine tetraacetate (EDTA), and benzyl alcohol. The preservative can be selected to avoid possible incompatibilities between the preservative and other ingredients. Preservatives are preferably employed in amounts ranging from about 0.01% to about 2% by weight of the composition. Other preservatives known in the art can be used in the present invention.

V.i.) Moisturizing Agents

Moisturizing agents which can be used in the present invention include glycerol, sodium pyrrolidonecarboxylate, NMFs (normal moisturizing factors) and hyaluronic acid.

VI. PROCESSING METHOD

The particle-making procedures are described generally in Nixon (ed.), Microencapsulation, pp. 13–38 (Marcel Dekker, Inc. 1976); Muller, Colloidal Carriers for Controlled Drug Delivery and Targeting, pp. 175–202 (CRC Press 1991); Shaw (ed.), Lipoproteins as Carriers of Pharmacological Agents, pp. 97–139 (Marcel Dekker, Inc. 1991); and Benita (ed.), Microencapsulation—Methods and Industrial applications, pp. 183–258 (Marcel Dekker, Inc. 1996).

The process for producing the nano-particles comprises the steps of:

(i) heating the hydrophobic polymers and copolymers to a temperature above the material melting point;

(ii) dissolving or dispersing the active agents and/or the sensory markers into the melt;

(iii) dissolving or dispersing the cationic conditioning agents and/or cationic charge boosters in the melt;

(iv) optionally dissolving or dispersing the cationic conditioning agents, cationic charge boosters, and a co-surfactant in the aqueous phase and heating it to a temperature above the melting point of the melt;

(v) mixing the hot melt with the aqueous solution to form a suspension;

(vi) high shear homogenization of the suspension at a temperature above the melting temperature until a homogeneous fine suspension is obtained; and (vii) cooling the suspension to ambient temperature to create a fine dispersion.

The melt phase is dispersed into the aqueous phase by agitation, such as with an ultrasonic processor, high pressure homogenizer, colloid mill, or high sheer mixer until small, fairly uniform size particles are formed. The dispersion is then cooled to at least room temperature to form the final suspension of hydrophobic phase particles within the continuous aqueous phase.

The fairly uniform particles formed within the aqueous phase should be less than about 2 microns, preferably have number average diameters of less than about 1 micron, more preferably have number average diameters of less than about 0.5 microns, and most preferably have number average diameters of between about 0.01 and about 0.5 microns, with about 0.1 to about 1 microns being particularly preferred.

The method of preparation of nano-particles described herein is simple and is characterized by high loading, reproducibility, versatility, and stability. The method is further illustrated in the non-limiting examples.

The active agents and sensory markers that are dissolved within in the nano-particles can be released by molecular diffusion at a rate according to Fick's second law of diffusion described in "Diffusion in Polymers", Crank J. and Park G. S., Academic Press, New-York, 1969; "Barriers Polymers and Structures", Edited by Koros W. J., ACS Series, Washington DC, 1990; "Polymer Permeability", Edited by J. Comyn, Elsevier Applied Science publishers, 1985 pp. 217–267; incorporated herein as references:

$$\frac{\partial C}{\partial t} = \frac{\partial}{\partial X}\left(D\frac{\partial C}{\partial X}\right) = D\frac{\partial^2 C}{\partial X^2}$$

where:
D=diffusion coefficient
C=concentration of the diffusing molecule
X=direction of diffusion
t=time Higuchi has developed equations for spherical monolithic devices having homogenous matrices (Higuchi T., J. Pharm. Sci., 52, 1145, 1963). The theoretical early and late time approximation of the release rate of the active ingredients dissolved in the hydrophobic matrix of the nano particles can be calculated from the following equations:

Early time approximation $(m_t/m_\infty) < 0.4$ $$\frac{M_t}{M_\infty} = 6\left[\frac{Dt}{r^2\pi}\right]^{1/2} - \frac{3Dt}{r^2}$$

Late time approximation $(m_t/m_\infty) > 0.6$ $$\frac{M_t}{M_\infty} = 1 - \frac{6}{\pi^2}\exp\left[\frac{-\pi^2 Dt}{r^2}\right]$$

Where;
r—the radius of the cylinder
$m_\infty$—the amount of active released from the controlled release system after infinite time
$m_t$—the amount of active released from the controlled release system after time t
D—the diffusion coefficient of the fragrance or aroma chemical in the polymer Brophy and Deasy (Brophy M. and and Deasy p B., Int. J. Pharm., 37, 41, 1987) developed an equation based on the pseudo steady state approximation of Higuchi. The equation derived describes the release of a dispersed solute from a rigid sphere matrix where there is no swelling or erosion of the matrix.

$$M_t = A[DCs(2CO - Cs)t]^{1/2} - \frac{4}{9}8\pi r DCs\frac{3Co - 2Cs}{2Co - Cs}t$$

Where:
Co is active concentration in the microparticles
Cs is the active solubility (the saturation concentration)
r is the radius of the sphere

VII. PARTICLE ADHESION ONTO HAIR

Figure 2:
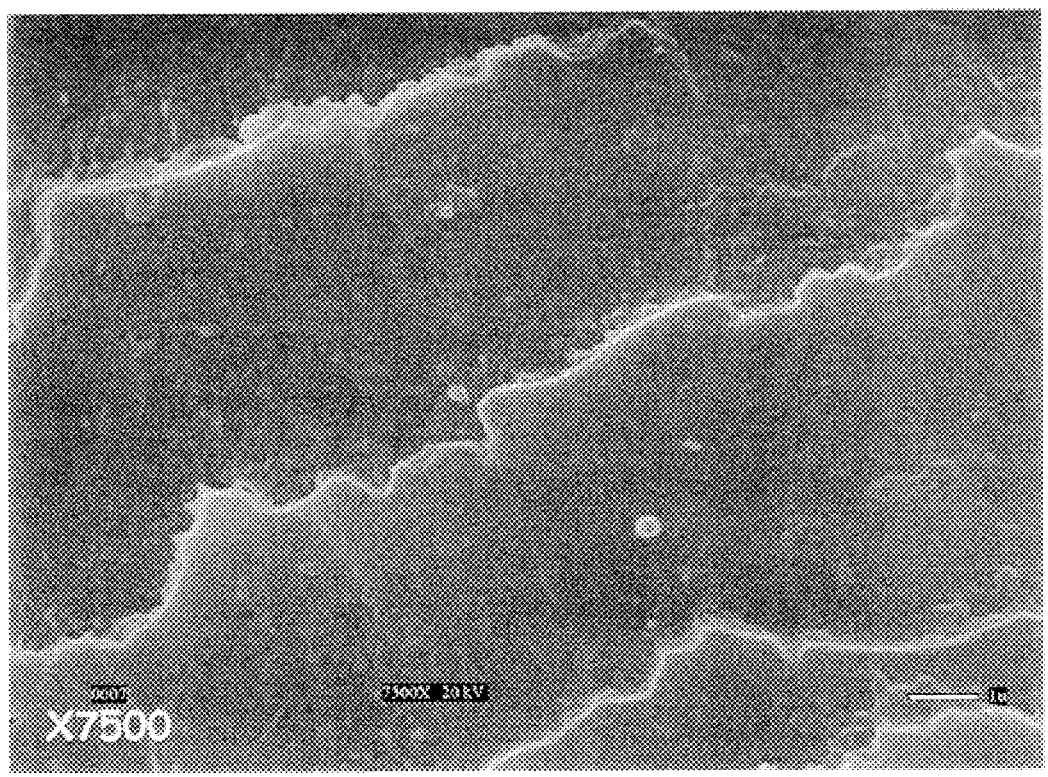
FIG. 2 is a scanning electron microscopy image of hair, treated with a conditioner comprising the nano-particle of the present invention, magnified 7500 times.
Figure 3:
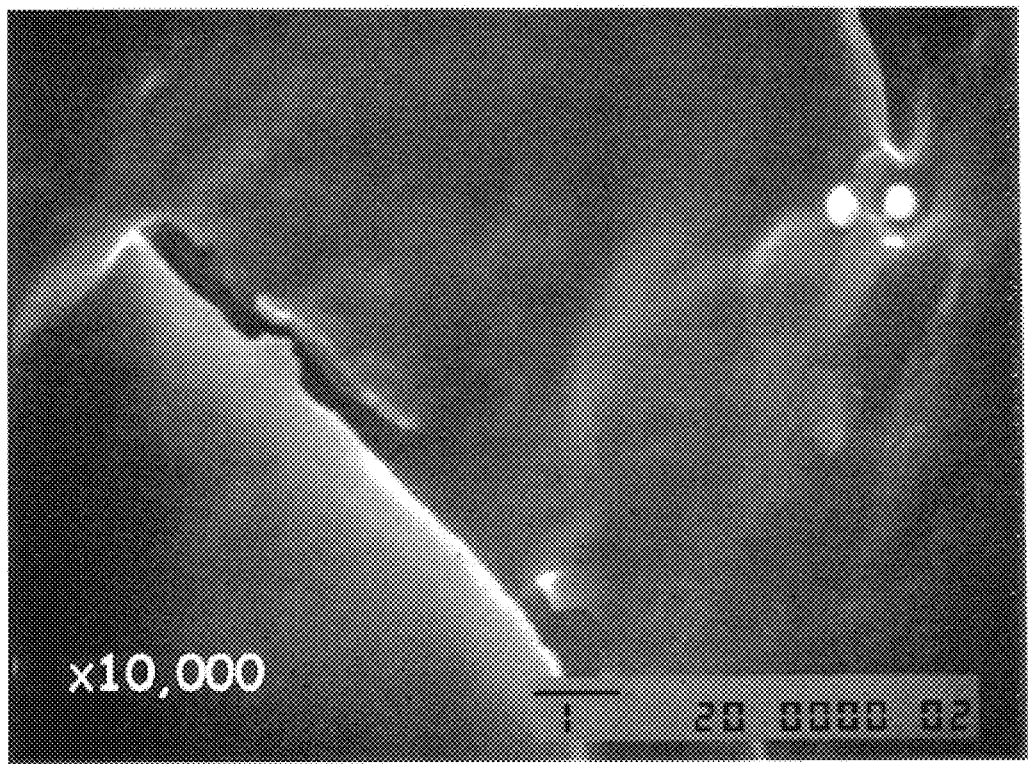
FIG. 3 is a scanning electron microscopy image of hair, treated with a conditioner comprising the nano-particle of the present invention, magnified 10,000 times.

The substantivity of the nano-particles of the present invention was determined by examining hair samples treated with hair care products comprising the nano-particles of the present invention under a scanning electron microscope (SEM). The substantivity of the nano-particles of example 1 onto hair, from a shampoo application is shown in FIG. 1. FIG. 1 illustrates scanning electron microscopy image of hair, treated with a shampoo comprising the nano-particle of the present invention, magnified 7500 times. The substantivity of the nano-particles of example 2 onto hair, from a conditioner application is shown in FIG. 2 and FIG. 3. FIG. 2 illustrates a scanning electron microscopy image of hair, treated with a conditioner comprising the nano-particle of the present invention, magnified 7500 times. FIG. 3 illustrates a scanning electron microscopy image of hair, treated with a conditioner comprising the nano-particle of the present invention, magnified 10,000 times.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

SAMPLE PREPARATION

EXAMPLE 1

The fragrance used in the following examples is a fragrance composition that is not substantive on hair when used as neat oil. The fragrance composition used is as follows:

| Perfume Composition | Component (% Wt.) |
| --- | --- |
| Geraniol | 30.0 |
| Dihydro Myrcenol | 20.0 |
| Phenyl Ethyl Alcohol | 5.0 |
| Linalool | 25.0 |
| Tetrahydro Linalyl Acetate | 20.0 |

The nano-particles had the following compostion; Incroquat Behenyl HE, behenamidopropyl hydroxyethyl dimonium chloride (a fatty quaternary ammonium salt, commercially available from Croda) was used as cationic conditioning agent, LUPASOL™ PR815, a polyethyleneimine having an average molecular weight of 1800 (commercially available from BASF Corporation) was used as a cationic charge booster, and Tween 20 was used as a co-surfactant. The hydrophobic polymer was candelilla/silicon copolymer (commercially available from Strahl & Pitsch Inc.) The suspension is homogenized using an APV, Rannie 2000 High Pressure Homogenizer. The resulting formulation is:

48.9% water
15% candelilla/silicon copolymer
20% Vitamin E
10% Menthol;
1% Incroquat Behenyl HE
0.1% LUPASOL™PR815
5% Teen 20

300 grams of candelilla/silicon copolymer is placed in an oven at 120 degrees C and allowed to melt. 978 grams of deionized water is placed into one gallon vessel of the homogenizer, that fitted with a all-purpose silicon rubber heater (Cole-Palmer Instrument Company). 100 grams of Tween 20 are added to the water and the aqueous solution is heated to 90 degrees C while mixing it with a propeller mixer. The candelilla/silicon copolymer melt is removed from the oven, 20 grams of Incroquat Behenyl HE, 2 grams of LUPASOL™ PR815, 200 grams of menthol, and 400 grams of vitamin E are mixed into the candelilla/silicon copolymer melt by hand with a glass rod. The melt mixture is than poured into the vessel containing aqueous solution and the emulsion is homogenized at 20,000 psi. The dispersion is cooled to ambient temperature by passing it through a tube-in-tube heat exchanger (Model 00413, Exergy Inc. Hanson Mass.).

The shape and size of the nano-particles was verified by examining the samples under a scanning electron microscope (SEM). SEM studies showed that the nano-particles of Example 1 are spherical in nature with an average particle size of approximately 0.1 microns to 0.5 microns.

The nano particles obtained were incorporated into a shampoo base (Example 3). Hair swatches were washed with the shampoo comprising the nano particles of the present invention. The hair swatches were left to air dry for 24 hours and the ability of the nano particles to adhere to hair was determined by SEM. The results, shown in FIG. 1, clearly demonstrate that the nano-particles deposit and adhere onto hair and are not washed off during the rinse process.

EXAMPLE 2

The nano-particles had the following compostion; Incroquat Behenyl HE, behenamidopropyl hydroxyethyl dimonium chloride (a fatty quaternary ammonium salt, commercially available from Croda) was used as cationic conditioning agent and LUPASOL™PR815, a polyethyleneimine having an average molecular weight of 1800 (commercially available from BASF Corporation) was used as a cationic charge booster. The hydrophobic polymer was polyethylene homo-polymer (commercially available from Allied Signal Inc.) The suspension is homogenized using an APV, Rannie 2000 High Pressure Homogenizer. The resulting formulation is:

68.9% water;
15% polyethylene;
15% fragrance;
1% Incroquat Behenyl HE
0.1% LUPASOL™PR815

300 grams of polyethylene polymer is placed in an oven at 150 degrees C and allowed to melt. 1378 grams of deionized water is placed into one gallon vessel of the homogenizer, that fitted with a all-purpose silicon rubber heater (Cole-Palmer Instrument Company). 20 grams of Incroquat Behenyl HE and 2 grams of LUPASOL™PR815 are added to the water and the aqueous solution is heated to 95 degrees C while mixing it with a propeller mixer. The polyethylene polymer is removed from the oven 300 grams of fragrance are mixed into the polyethylene polymer by hand with a glass rod. The melt mixture is than poured into the vessel containing aqueous solution and the emulsion is homogenized at 20,000 psi. The dispersion is cooled to ambient temperature by passing it through a tube-in-tube heat exchanger (Model 00413, Exergy Inc. Hanson Mass.).

The shape and size of the nano-particles was verified by examining the samples under a scanning electron microscope (SEM). SEM studies showed that the nano-particles of Example 2 are spherical in nature with an average particle size of approximately 0.1 microns to 0.5 microns.

The nano particles obtained were incorporated into a conditioner base (Example 3). Hair swatches were washed with the conditioner comprising the nano particles of the present invention. The hair swatches were left to air dry for 24 hours and the ability of the nano particles to adhere to hair was determined by SEM. The results, shown in FIG. 2 and FIG. 3, clearly demonstrate that the nano-particles deposit and adhere onto hair and are not washed off during the rinse process.

EXAMPLE 3

Use of Shampoo

The ability of the nano particles of Example 1 to extend the release of active agents and sensory markers (menthol) was determined by evaluating the menthol odor intensity retained on hair washed with a shampoo composition comprising the nano particles of example 1.

10 grams of the suspension of Example 1 is admixed with 90 grams of a shampoo base (30% concentrated shampoo base #4, product of JEEN International Corporation, of Little Fall, N.J. and 70% water) to create a shampoo sample containing 1.0% menthol and 2% vitamin E. A control sample was created by admixing 1.0 gram of menthol and 2 grams of vitamin E with the above shampoo base.

Four hair swatches were washed with the shampoo sample comprising the nano-particles of Example 1 and four hair swatches were washed with the control sample comprising the neat menthol.

Two of the hair swatches in each experimental set (two washed with the shampoo comprising the nano-particles and two washed with the control sample) were dried using a blow dryer. The intensity of the menthol retained on the wet swatches and the odor emitted 1 minute after drying the hair with a blow dryer was evaluated using a scale of 1 to 10, where 1 measures a low odor intensity and odor intensity of 10 measures a high intensity, pleasant odor. Odor perception is, by its nature, a very subjective determination and therefore needs to be determined by a panel of trained odor evaluator. According to the procedure, the hair swatches tested were provided to a panel of six odor evaluators who independently rank odor intensity retained on the wet hair swatches and in the proximate environment, 1 minute after blow drying the hair. The odor evaluation results were as follow:

|  | Wet Hair | One Minute After Blow-Drying |
| --- | --- | --- |
| Neat Menthol (Control) | 3 | 4 |
| Menthol in Nano Particles | 5 | 8 |

These results show that the hair swatches washed with the control samples, comprising the neat menthol, had very low odor intensity. The hair swatches washed with the shampoo comprising the menthol in the nano particles had higher odor intensity. Thus, the nano particles of the present invention adhere to hair and can be utilize to deposit higher level of fragrance onto hair. Only the hair swatches washed with the shampoo comprising the nano-particles provided high impact menthol "burst" upon blow drying the hair. Thus, the nano particles of the present invention have the ability to provide heat triggered release of the active agents and yield high impact odor "burst" upon blow drying the hair or other type of heat treatment.

The other four hair swatches (washed with the shampoo comprising the nano-particles and the control sample) were air-dried and odor intensity of the menthol retained on the dry swatches was evaluated after one hour and after 8 hours using the same scale as above. According to the procedure, the hair swatches to be tested were provided to a panel of six odor evaluators who independently rank odor intensity retained on the hair swatches. The odor evaluation results after one hour and after 8 hours, on the dry hair swatches were as follow:

|  | Neat Menthol (Control) | Menthol in Nano Particles |
| --- | --- | --- |
| One Hour | 4 | 2 |
| 8 Hours | 4 | 1 |

These results show that the hair swatches washed with the control samples, comprising the neat menthol, had very low odor intensity. The hair swatches washed with the shampoo comprising the menthol in the nano particles had higher odor intensity. Thus, the nano particles of the present invention adhere to hair and can be utilize to deposit higher level of fragrance onto hair. Odor intensity of the hair swatches washed with the shampoo comprising the fragrance in the nano particles, after 8 hours, was significantly higher than that of the swatches washed with these products comprising the neat menthol. Also, Odor intensity of the hair swatches washed with the shampoo comprising the menthol in the nano particles, remain the same after as after one hour. Thus, the nano particles of the present invention have the ability to sustain the release of active ingredients and provide extended release, even for volatile ingredients such as menthol. The release rate of the menthol, or other sensory markers, can be synchronize with that of the active agent, i.e., vitamin E in this example, to convey to the consumer the product performance.

EXAMPLE 4

Use of Conditioner

The ability of the nano particles of Example 2 to extend the release of active agents and sensory markers (i.e., a fragrance) was determined by evaluating the odor intensity retained on hair washed with a hair conditioner composition comprising the nano particles of example 2.

10 grams of the suspension of Example II is admixed with 90 grams of a conditioner base (40% Jeequat ASP, product of JEEN International Corporation, of Little Fall, N.J. and 60% water) to create a hair conditioner sample containing 1.5% fragrance. A control sample was created by admixing 1.5 grams of the neat fragrance with the above conditioner base.

Two hair swatches were washed with the conditioner sample comprising the nano particles of Example II and two hair swatches were washed with the control sample comprising the neat fragrance. The hair swatches were air dried and odor intensity of the fragrance retained on the dry swatches was evaluated after one hour and after 24 hours. Odor perception is, by its nature, a very subjective determination. According to the procedure, the hair swatches to be tested were provided to a panel of six odor evaluators who independently rank odor intensity retained on the hair swatches using a scale of 1 (neutral, low odor intensity) to 10 (high, pleasant, odor intensity). The odor evaluation results after one hour and after 24 hours, on the dry hair swatches were as follow:

|  | Neat Fragrance (Control) | Fragrance in Nano Particles |
| --- | --- | --- |
| One Hour | 5 | 7 |
| 24 Hours | 3 | 8 |

These results show that the hair swatches washed with the control samples, comprising the neat fragrance, had very low odor intensity. The hair swatches washed with the conditioner comprising the fragrance in the nano particles had higher odor intensity. Thus, the nano particles of the present invention are adhere to hair and can be utilize to deposit higher level of fragrance onto hair. Odor intensity of the hair swatches washed with the conditioner comprising the fragrance in the nano particles, after 24 hours, was significantly higher than that of the swatches washed with these products comprising the neat fragrance. Also, Odor intensity of the hair swatches washed with the conditioner comprising the fragrance contained in the nano particles, was almost as high as their odor intensity after one hour. Thus, the nano particles of the present invention have the ability to sustain the release of active ingredients and provide extended release, even for volatile ingredients such as fragrances. The release rate of the fragrance, or other sensory markers, can be synchronize with that of ascorbic acid, or other active ingredients, to convey to the consumer the product performance.

It is understood that the above-described embodiments are illustrative of only a few of the many possible specific embodiments which can represent applications of the principles of the invention. Numerous and varied other arrangements can be readily derived in accordance with these principles by those skilled in the art without departing from the spirit and scope of the invention.

What is claimed is:

1. A controlled delivery system for topical application to hair comprising:
    a solid particle comprising an active agent, a cationic charge booster and a cationic conditioning agent,
    said cationic charge booster is selected from the group consisting of polyvinyl amine, polyamine, polyalkyleneamine, polyalkyleneimine, a polyquaternary ammonium compound and a quaternary ammonium compound having the formula,

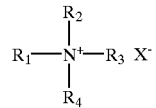

wherein X is an anion and $R_1$, $R_2$, $R_3$, and $R_4$ are each independently $C_{1-C22}$ alkyl, $C_3-C_{22}$ alkenyl, or $R_5$—Q—$(CH_2)_m$—, wherein $R_5$ is $C_1-C_{22}$ alkyl or alkenyl moiety having from 1 to 22 carbon atoms, and mixtures thereof, m is from 1 to about 6;
    and when taken together with the Q unit is an acyl unit, Q can be derived from a source of triglyceride selected from the group consisting of tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof.

2. The system of claim 1 wherein said solid particle further comprises a hydrophobic polymer, hydrophobic copolymer, or a mixture thereof.

3. The system of claim 2 wherein said particle has a melting point between about 40 degrees C to about 100 degrees C.

4. The system of claim 2 wherein said hydrophobic polymer or hydrophobic copolymer is selected from a group consisting of: polyethylene homopolymers; ethylene-acrylic acid copolymer; polyamide polymer having a molecular weight in the range of from about 6,000 up to about 12,000; polyethylene-vinyl acetate copolymer; silicon synthetic wax copolymer; silicon natural wax copolymer; candelilla silicon copolymer, ozokerite silicon copolymer; siliconyl candelilla copolymer; and siliconyl synthetic paraffin copolymer.

5. The system of claim 4 wherein said hydrophobic polymer comprises polyethylene.

6. The system of claim 4 wherein said hydrophobic copolymer comprises candelilla silicon copolymer.

7. The system of claim 4 wherein said hydrophobic copolymer comprises ozokerite silicon copolymer.

8. The release system of claim 1 where said particle has an average particle diameter of from about 0.01 micron to about 10 microns.

9. The system of claim 8 wherein said average particle diameter is from about 0.1 microns to about 1 micron.

10. The system of claim 1 wherein said cationic charge boosters comprises polyethyleneimine having an average molecular weight of 1,800.

11. The system of claim 1 wherein said cationic conditioning agents are selected from a group consisting of straight-chain alkylammonium compounds, cyclic alkylammonium compounds, petroleum derived cationic compounds, and cationic polymers.

12. The system of claim 1 wherein said cationic conditioning agent comprises cetyl trimethylammonium chloride.

13. The system of claim 1 wherein said cationic conditioning agent comprises behenamidopropyl hydroxyethyl dimonium chloride.

14. The system of claim 1 wherein said cationic conditioning agent comprises polyquaterium-24.

15. The system of claim 1 wherein said cationic conditioning agent comprises quaternium-82.

16. The system of claim 1 wherein said active agent is selected from the group consisting of ceraimides, vitamins, antioxidants, free radical scavengers, moisturizing agents, antiseborrhoeic agents, anti-UV agents, keratolytic agents, anti-inflammatory agents, refreshing agents, melanoregulators, liporegulators, antiseborrhoeic agents, anti-ageing agents, keratolytic agents, antibacterial agents, anti-dandruff agents, agents for combating hair loss, hair dyes, hair bleaches, reducing agents for permanent waves, hair conditioners, nutrients, cicatrizing agents, vascular protectors, antibacterial agents, anti fungal agents, skin conditioners, immunomodulators, nutrients, oils, retinoids, anesthetics, surfactants, emulsifiers, stabilizers, preservatives, antiseptics, emollients, lubricants, humectants, anesthetics, analgesics, enzymes, pigments, dyes, hydroxy acids, emollients, medications, antibiotics, repellants, attractants, fragrances, sensory markers, hyaluronic acid, hyaluronic acid salts, elastins, hydrolysates, primrose oil, jojoba oil, epidermal growth factor, soybean saponins, mucopolysaccharides, and mixtures thereof.

17. The system of claim 1 wherein said active agent comprises a fragrance.

18. The system of claim 1 further comprising a co-surfactant selected from the group consisting of: phospholipids, polysorbates, polyethylene glycol esters of fatty acids, polyethoxylated fatty acid, stearic acid, polyethoxylated isooctylphenol/formaldehyde polymer; poloxamers, poly(oxyethylene)poly(oxypropylene) block copolymers, polyoxyethylene fatty alcohol ethers, polyoxyethylene nonylphenyl ethers, and polyoxyethylene isooctylphenyl ethers.

19. The system of claim 1 wherein said hydrophobic polymer, hydrophobic copolymer or mixture thereof is present in an amount of about 1% to about 95% by weight, said cationic charge booster is present in an amount of about 0.1% to about 10% by weight, said cationic conditioning agents are present in an amount of about 0.01% to about 20/o by weight, and said active agent is present in an amount of about 1% to about 70%A by weight.

20. The system of claim 1 further comprising about 1% to about 70% by weight of a sensory marker.

21. The system of claim 1 wherein said particles release said cationic charge booster and said cationic conditioning agent over an extended period of time.

22. The system of claim 1 wherein said extended period of time is up to about 24 hours.

23. The system of claim 1 wherein said particle releases an effective amount of said cationic charge booster and said cationic conditioning agent to provide a burst upon heat treatment of said particle.

24. The system of claim 1 wherein said hydrophobic material is selected from the group consisting of natural waxes, synthetic waxes, fatty acid esters, fatty alcohols, solid hydrogenated plant oils, biodegradable natural polymers and synthetic polymers.

25. A method of producing a controlled release system for topical application to hair comprising the steps of:

heating a matrix material of a hydrophobic polymer to a temperature above the material melting point;

dissolving or dispersing an active agent into the melt;

dissolving or dispersing a cationic conditioning agent and cationic charge booster into the melt, said cationic charge booster is selected from the group consisting of polyvinyl amine, polyamine, polyalkyleneamine, polyalkyleneimine, a polyquaternary ammonium compound and a quaternary ammonium compound;

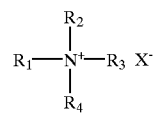

wherein X is an anion and $R_1$, $R_2$, $R_3$, and $R_4$ are each independently $C_1$–$C_{22}$ alkyl, $C_3$–$C_{22}$ alkenyl, or $R_5$—Q—$(CH_2)_m$—, wherein $R_5$ is $C_1$–$C_{22}$ alkyl or alkenyl moiety having from 1 to 22 carbon atoms, and mixtures thereof, m is from 1 to about 6;

and when taken together with the Q unit is an acyl unit, Q can be derived from a source of triglyceride selected from the group consisting of tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof, heating the melt to a temperature above the melting point of the melt;

mixing the hot melt with the aqueous solution to form a suspension;

high shear homogenization of the suspension at a temperature above the melting temperature until a homogeneous fine suspension is obtained; and cooling the suspension to ambient temperature to create a fine dispersion.

26. The method of claim 25 further comprising before the step of heating the melt the step of:

dissolving or dispersing a co-surfactant in the melt.

27. A hair care product comprising the system of claim 1.

28. The hair care product of claim 27 is selected from the group consisting of:

shampoo, conditioners and hair styling products.

29. The hair care product of claim 28 where the release of said active agent is activated by heat treatment of the hair.

30. The hair care product of claim 29 further comprising a sensory marker.

31. The hair care product of claim 30 wherein the release of said active agent is activated by heat treatment of the hair.

* * * * *